(12) United States Patent
Hickey

(10) Patent No.: US 9,914,945 B2
(45) Date of Patent: Mar. 13, 2018

(54) PROCESSES FOR BIOCONVERTING SYNGAS TO OXYGENATED HYDROCARBONACEOUS COMPOUNDS

(71) Applicant: Coskata, Inc., Warrenville, IL (US)

(72) Inventor: Robert Hickey, Okemos, MI (US)

(73) Assignee: Synata Bio Inc., Warrenville, IL (US)

( * ) Notice: Subject to any disclaimer, the term of this patent is extended or adjusted under 35 U.S.C. 154(b) by 46 days.

(21) Appl. No.: 14/671,834

(22) Filed: Mar. 27, 2015

(65) Prior Publication Data

US 2016/0281115 A1 Sep. 29, 2016

(51) Int. Cl.
| | | |
|---|---|---|
| C12P 7/06 | (2006.01) | |
| C12P 7/04 | (2006.01) | |
| C12P 7/16 | (2006.01) | |
| C12P 7/14 | (2006.01) | |
| C12N 1/20 | (2006.01) | |

(52) U.S. Cl.
CPC .................. *C12P 7/16* (2013.01); *C12N 1/20* (2013.01); *C12P 7/04* (2013.01); *C12P 7/065* (2013.01); *C12P 7/14* (2013.01); *Y02E 50/10* (2013.01); *Y02E 50/17* (2013.01)

(58) Field of Classification Search
None
See application file for complete search history.

(56) References Cited

U.S. PATENT DOCUMENTS

| | | |
|---|---|---|
| 2014/0051139 A1 | 2/2014 | Lokken |
| 2014/0273125 A1 | 9/2014 | Hickey et al. |

FOREIGN PATENT DOCUMENTS

| | | | | |
|---|---|---|---|---|
| WO | WO 2011/139163 | * 11/2011 | ................ | C12P 7/06 |
| WO | 2014088427 A1 | 6/2014 | | |

OTHER PUBLICATIONS

Sullivan et al., Fertilizing with Biosolids, PNW 508-E, Revised Jun. 2007, Available Online at: www.ecy.wa.gov/programs/swfa/biosolids/pdf/Fertilizing.pdf.*
Flickinger, Ed., Downstream Industrial Biotechnology Recovery and Purification, Chapter 32: Membrane Separations, 32.4 Classification of Membranes and Membrane Processes, 2013, John Wiley & Sons, Inc.: Hoboken, New Jersey.*
Jae-Sok Kim et al, "Distillery waste recycle through membrane filtration in batch alcohol fermentation," Biotechnology Letters, vol. 21, No. 5, 1999, pp. 401-405, XP002757660.
Lapisova K et al, "Separation techniques for distillery treatment," Czech Journal of Food Sciences, vol. 24, No. 6, 2006, pp. 261-267, XP002757661.

* cited by examiner

*Primary Examiner* — Karen Cochrane Carlson
*Assistant Examiner* — Jennifer M. H. Tichy
(74) *Attorney, Agent, or Firm* — Cardinal Law Group

(57) ABSTRACT

Continuous processes for the anaerobic bioconversion of syngas to oxygenated hydrocarbonaceous products, in particular lower alkanols, are disclosed in which nutrients, including micronutrients, and lower carboxylate anion are recovered from at least a portion of an aqueous distillation fraction from a distillation unit operation to recover lower alkanols by using a "tight" ultrafiltration membrane. At least about 75 percent of the water permeates the ultrafiltration membrane. The tight ultrafiltration membrane rejects sufficient components that are adverse to the microorganisms used in the bioconversion that continuous fermentation operations over long durations can be achieved.

20 Claims, 1 Drawing Sheet

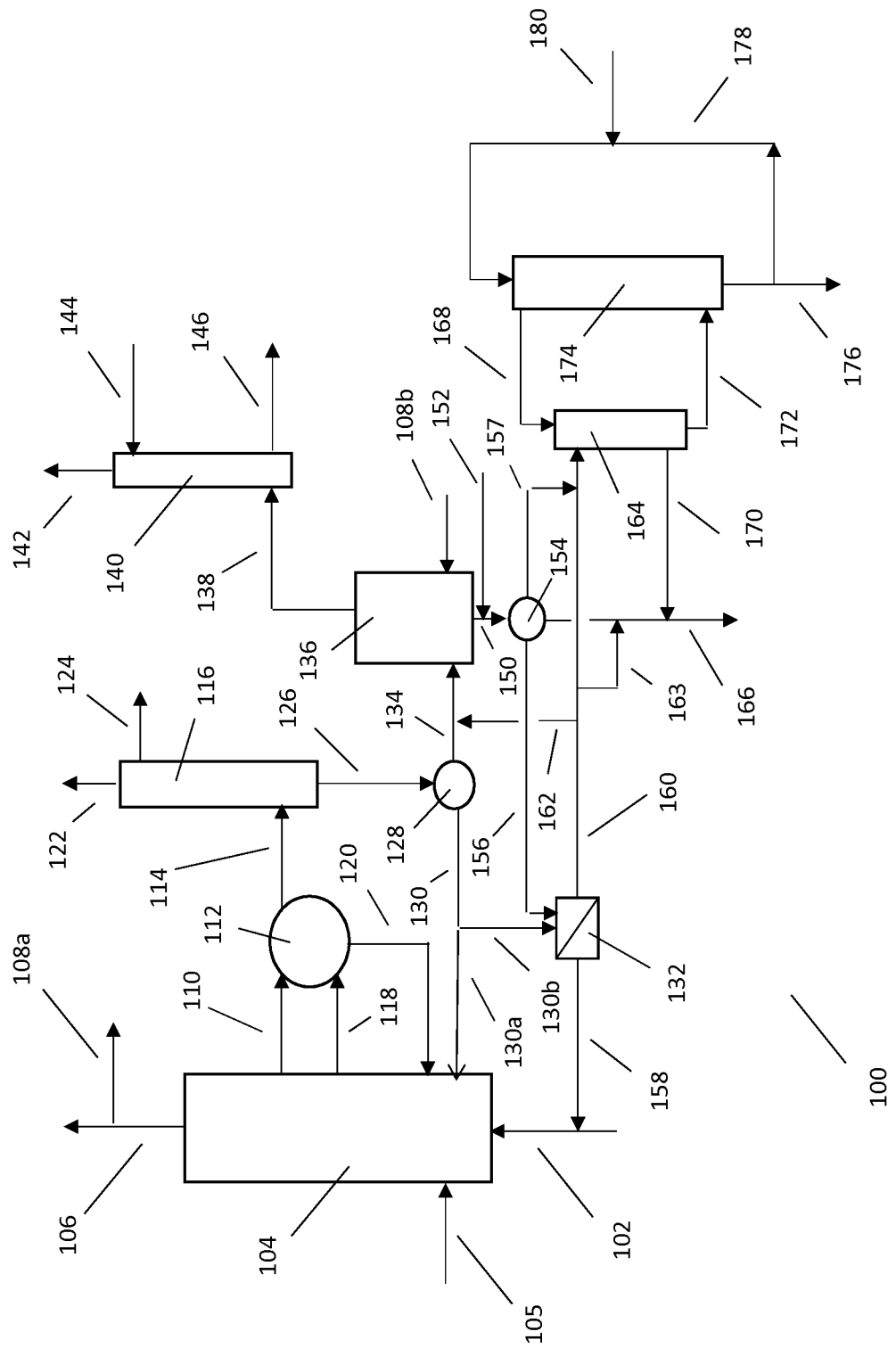

PROCESSES FOR BIOCONVERTING SYNGAS TO OXYGENATED HYDROCARBONACEOUS COMPOUNDS

FIELD OF THE INVENTION

This invention pertains to continuous, commercial processes for the anaerobic bioconversion of syngas to oxygenated hydrocarbonaceous compounds, especially lower alkanol having enhanced bioconversion efficiencies.

BACKGROUND

Anaerobic fermentations of hydrogen and carbon monoxide involve the contact of a gaseous substrate-containing feed with an aqueous fermentation broth containing microorganisms capable of generating oxygenated hydrocarbonaceous compounds, most commonly lower alkanols such as ethanol, propanol and n-butanol. The bioconversion of carbon monoxide results in the production of oxygenated hydrocarbonaceous compounds and in many cases a lower alkanol and carbon dioxide. The conversion of hydrogen involves the consumption of hydrogen and carbon dioxide, and this conversion is sometimes referred to as the $H_2/CO_2$ conversion or, as used herein, the hydrogen conversion.

Typically the substrate gas for carbon monoxide and hydrogen conversions is, or is derived from, a synthesis gas (syngas) from the gasification of carbonaceous materials, from the reforming of natural gas and/or biogas from anaerobic digestion or from off-gas streams of various industrial methods. The gas substrate contains carbon monoxide, hydrogen, and carbon dioxide and usually contains other components such as water vapor, nitrogen, methane, ammonia, hydrogen sulfide and the like. For the sake of convenience, the substrate gas is referred to herein as "syngas" even though it may only contain one of carbon monoxide and hydrogen and may not be derived by the gasification of carbonaceous materials.

These anaerobic fermentation processes are suitable for continuous processes. The syngas is passed into a bioreactor the aqueous fermentation broth for the bioconversion. Off gases can be removed from the bioreactor, and aqueous broth can be withdrawn from the bioreactor for recovery of the oxygenated hydrocarbonaceous compounds or lower alkanol at a rate sufficient to maintain steady-state operation. For the anaerobic fermentations to be commercially viable, economies of scale are required. Hence, commercial scale reactors, i.e., those with liquid capacities of at least 1 million, and more often at least about 5, say, 5 to 25, million, liters would be advantageous.

In the production of lower alkanol in these commercial-scale processes, broth is withdrawn at a rate sufficient to maintain the lower alkanol at concentrations below those that adversely affect the microorganisms used for the bioconversion. Typically the concentration of the alkanol in the fermentation broth is below about 5 mass percent. Thus, a relatively dilute stream is processed to recover the lower alkanol, typically by a unit operation comprising distillation. The hydraulic retention time of the broth in the bioreactor is often less than about 3 days. Consequently, nutrients and micronutrients contained in the withdrawn broth can represent an economic loss. A commercial-scale process would thus seek to recycle water from the alkanol recovery operation. The portion of the water that can be recycled is limited as the syngas bioconversion processes produce metabolites and proteins can be present that can, in sufficient concentrations, adversely affect the microorganisms, e.g., be toxic or inhibitory to the microorganisms or affect metabolic pathways or cause a metabolic shift.

Peyton, et al., in U.S. Pat. No. 7,569,146, disclose, in connection with drawing 3, processes for obtaining potable water from still bottoms in the bioconversion of starch and sugars to ethanol. As shown in the drawing, the still bottoms is subjected to pressurized filtration, with the retentate, which contains carbohydrates, being passed to an enzymatic conversion unit operation (29a), and the enzymatic product is subjected to pressurized filtration where the sugars permeate the membrane and the retentate is sent to anaerobic digestion in CSTR reactor 32. The permeate, containing the sugars, is passed via line 29d to the ethanol fermentation. The patentees on drawing 3 caption the pressurized filtration as "MF/UF/NF"; however, they clearly state that the fermentable sugars pass through the membrane. As shown, at least two pressurized filtrations are used by Peyton, et al., where sugars are recovered and recycled to the ethanol fermentation, and the capital and operating costs offset the value of the incremental sugars being passed to the ethanol fermentation.

Although Peyton, et al., disclose the use of pressurized filtration in certain fermentation processes, they provide no disclosure or suggestion regarding reducing nutrient and micronutrient loss for anaerobic syngas fermentation processes or increasing the amount of water that can be recycled to the bioreactor in a syngas fermentation without undue adverse effect on the microorganisms or the bioconversion activity.

Accordingly, continuous processes are sought to reduce nutrient and micronutrient loss in the anaerobic bioconversion of syngas to oxygenated hydrocarbonaceous products which processes can be economically practiced on a commercial scale.

SUMMARY OF THE INVENTION

By this invention, continuous processes for the anaerobic bioconversion of syngas to oxygenated hydrocarbonaceous compounds, such as alkanols are provided that can be practiced on a commercial-scale in an economically advantageous manner. In accordance with the processes of this invention, nutrients and micronutrients for the syngas fermentation are recovered from liquid normally discharged, or purged, from the process and returned to the fermentation reactor together with a portion of the water in the liquid discharge. The processes can be practiced over extended durations of time without undue risk of a build-up of components in the fermentation broth that could adversely affect the fermentation. Additionally, lower carboxylate anion, such as acetate and propionate, can be recovered from the liquid discharge and recycled to the syngas fermentation. The metabolic formation of these carboxylate anions is a diversion of syngas to other than the sought compounds, and thus represents a bioconversion inefficiency. The recycle of these carboxylate anions to the fermentation broth enables the microorganisms to use the carboxylate anions as a substrate. In most instances, although the microorganisms continue to utilize a carboxylate pathway, the concentration of the carboxylate anion in the fermentation broth remains relatively constant despite the introduction of carboxylate anion to the fermentation broth.

By this invention, it has been found that "tight" ultrafiltration can recover at least about 75, and often at least about 85 or 90, percent of the water contained in the liquid discharge from the aqueous distillation fraction. The tight ultrafiltration uses an ultrafiltration membrane having a cut-off in the range of from about 750 to 8000, preferably between about 800 and 7500, Daltons. The ultrafiltration membrane cut-off is thus sufficiently high that permeation of at least 75 percent of the water in the liquid discharge can be effected in a commercial-scale facility yet provide adequate selective rejection of sufficient metabolites and proteins that these metabolites and proteins do not build-up to a concentration in the fermentation broth that results in material adverse effects on the microorganisms used in the continuous fermentation of syngas. The tight ultrafiltration membranes, however, permit permeation of many of the nutrients and micronutrients contained in the aqueous distillate fraction as well as lower carboxylate anion. In the case of lower alkanols, due to the large fraction of the water in the aqueous distillate fraction that can be recycled to the fermentation broth, material reduction in the fresh nutrient and micronutrient supply to the fermentation broth can be achieved and efficiency of conversion of syngas to alkanol can be enhanced. Since a tight ultrafiltration membrane is used, the energy consumption per unit volume of permeate is typically appreciably less than that required for reverse osmosis. Moreover, the tight ultrafiltration membrane is somewhat less subject to fouling due to the presence of solids such as microorganisms and fragments of microorganisms in the liquid discharge.

In its broad aspects, the continuous processes of this invention for the anaerobic bioconversion of a gas substrate comprising carbon monoxide, hydrogen and carbon dioxide in an aqueous broth containing microorganisms suitable for converting said substrate to lower oxygenated hydrocarbonaceous compounds, which processes comprise:

a. continuously contacting said gas substrate with said aqueous broth under acidic, anaerobic fermentation conditions including the presence of nutrients to bioconvert gas substrate to oxygenated hydrocarbonaceous compounds and provide a oxygenated hydrocarbonaceous compounds-containing broth and a depleted gas phase, said anaerobic fermentation conditions also producing an co-produced, lower carboxylate anion and metabolites adverse to said microorganisms;

b. continuously withdrawing the depleted gas phase from said aqueous broth;

c. continuously or intermittently withdrawing a portion of said broth for recovery of said oxygenated hydrocarbonaceous compounds, said withdrawal being sufficient to maintain the oxygenated hydrocarbonaceous compounds in said broth below a concentration that unduly adversely affects the microorganisms;

d. continuously separating by distillation oxygenated hydrocarbonaceous compounds from the withdrawn portion of said broth to provide at least one fraction rich in said at least one oxygenated hydrocarbonaceous compound and an aqueous distillation fraction containing said at least one co-produced carboxylate anion and said adverse metabolites, wherein said distillation denatures said broth and generates free proteins;

e. optionally recycling a portion of the aqueous distillation fraction to step (a);

f. subjecting at least a portion of the aqueous distillation fraction to ultrafiltration to permeate at least about 75 percent of the water contained in said remaining portion, said ultrafiltration using an ultrafiltration membrane having a cut-off in the range of between about 750 and 8000 Daltons to provide a permeate; and g. recycling the permeated water of step (f) to step (a).

In its more specific aspects, the continuous processes of this invention for the anaerobic bioconversion of a gas substrate comprising carbon monoxide, hydrogen and carbon dioxide in an aqueous broth containing microorganisms suitable for converting said substrate to lower alkanol, which processes comprise:

a. continuously contacting said gas substrate with said aqueous broth under acidic, anaerobic fermentation conditions including the presence of nutrients to bioconvert gas substrate to lower alkanol and provide a lower alkanol-containing broth and a depleted gas phase, said anaerobic fermentation conditions also producing an co-produced, lower carboxylate anion and metabolites adverse to said microorganisms;

b. continuously withdrawing the depleted gas phase from said aqueous broth;

c. continuously or intermittently withdrawing a portion of said broth for recovery of said lower alkanol, said withdrawal being sufficient to maintain the lower alkanol in said broth below a concentration that unduly adversely affects the microorganisms;

d. continuously separating by distillation lower alkanol from the withdrawn portion of said broth to provide at least one fraction rich in said at least one lower alkanol and an aqueous distillation fraction containing said at least one co-produced carboxylate anion and said adverse metabolites, wherein said distillation denatures said broth and generates free proteins;

e. optionally recycling a portion of the aqueous distillation fraction to step (a);

f. subjecting at least a portion of the aqueous distillation fraction to ultrafiltration to permeate at least about 75 percent of the water contained in said remaining portion, said ultrafiltration using an ultrafiltration membrane having a cut-off in the range of between about 750 and 8000 Daltons to provide a permeate; and g. recycling the permeated water of step (f) to step (a).

Preferably, at least a portion of the withdrawn portion of the aqueous broth is subjected to a solids removal unit operation prior to being passed to step (d) and/or the aqueous distillation fraction is subjected to a solids removal unit operation prior to being passed to step (e), if used, or step (f), most preferably the solids removal unit operation is a density separation unit operation such as settling or centrifugation although filtration, such as microfiltration, can be used alone or in combination with a density separation unit operation. Where the solids removal unit operation is used, generally less than about 15, and preferably, less than about 10, say, 2 to 10, percent of the water being passed to the solids removal unit operation is contained in the solids-rich fraction. The solids-rich fraction may be purged or sent to an anaerobic digester. Thus, the removal of the solids in such a unit operation still enables the large majority of the co-produced, lower carboxylate and nutrients and micronutrients to be recovered and recycled to the aqueous fermentation broth.

In most instances, an aliquot portion of the aqueous distillation fraction can be recycled to the fermentation without undue build-up of adverse components. Where this option is used (step (e)), at least about 50, preferably at least about 60, up to about 85 or 90, percent of the aqueous distillation fraction is passed as an aliquot portion to the fermentation. The remaining portion (the liquid discharge) is the feed to the ultrafiltration unit operation.

The permeate of step (f) will contain co-produced, lower carboxylate anion and nutrients, including micronutrients. The concentration of each of these species in the permeate as compared to their concentration in the liquid discharge will reflect its permeation rate through the ultrafiltration membrane. Preferably, the permeate has a concentration of each of the potassium and ammonium cations of at least about 90 percent of that in the liquid discharge, and a concentration of sulfur and phosphorus-containing components of at least about 70 mass percent of that in the liquid discharge. In comparison, the concentration of proteins in the permeate is less than about 20 mass percent of that in the liquid discharge, and of total sugars, is less than about 35 mass percent of that in the liquid discharge.

BRIEF DESCRIPTION OF THE DRAWING

FIG. 1 is a schematic depiction of an apparatus for the anaerobic bioconversion of syngas to alkanol.

DETAILED DISCUSSION

All patents, published patent applications and articles referenced herein are hereby incorporated by reference in their entirety.

Definitions

As used herein, the following terms have the meanings set forth below unless otherwise stated or clear from the context of their use.

The use of the terms "a" and "an" is intended to include one or more of the element described.

Aqueous broth, or aqueous fermentation broth, means a liquid water phase which may contain dissolved compounds including, but not limited to hydrogen, carbon monoxide, and carbon dioxide. The broth may, but is not required, to contain microorganisms.

An aqueous distillation fraction is a still bottoms fraction or distillate fraction from a distillation unit operation which contains at least about 75 percent, preferably at least about 90, and often essentially all of, the water contained in the feed to the distillation assembly.

A bioreactor assembly is an assembly of one or more vessels suitable to contain aqueous broth and microorganisms for the bioconversion and can contain associated equipment such as injectors, recycle loops, agitators, and the like.

Biomass means biological material living or recently living plants and animals and contains at least hydrogen, oxygen and carbon. Biomass typically also contains nitrogen, phosphorus, sulfur, sodium and potassium. The chemical composition of biomass can vary from source to source and even within a source. Sources of biomass include, but are not limited to, harvested plants such as wood, grass clippings and yard waste, switchgrass, corn (including corn stover), hemp, sorghum, sugarcane (including bagas), and the like; and waste such as the organic fraction of municipal waste and municipal wastewater sludges. Biomass does not include fossil fuels such as coal, natural gas, and petroleum.

Fossil carbonaceous materials, or fossil fuels, include, but are not limited to, natural gas; petroleum including carbonaceous streams from the refining or other processing of petroleum including, but not limited to, petroleum coke; and lignite and coal.

Hydraulic retention time is the calculated residence time of a liquid in a vessel based upon flow rate and vessel volume.

Intermittently means from time to time and may be at regular or irregular time intervals.

Liquid discharge is the portion of the aqueous distillation fraction that is not recycled as an aliquot portion to the bioreactor assembly. The liquid discharge does not include any water lost with a solids separation unit operation.

Oxgenated hydrocarbonaceous compounds (referred to also as OHCs) comprise oxygen, carbon and hydrogen atoms as well as other hetero atoms and includes a more limited class of compounds defined as oxygenated hydrocarbons that only consist of oxygen, carbon and hydrogen atoms. In particular the oxygenated hydrocarbons are typically comprise ethers, alcohols, aldehydes and their associated ions.

Lower alkanol is monohydric, dihydric or trihydric compounds such as ethanol, propanol, butanol and butane diol.

Lower carboxylic anion is acetate, propionate and butyrate.

Microorganism retention time is the calculated residence time of microorganisms in a bioreactor and is greater than the hydraulic retention time where at least a portion of withdrawn fermentation broth is subjected to a unit operation to recover microorganisms that are recycled to the bioreactor assembly.

A nutrient is a source of carbon or hydrogen or nitrogen or oxygen or phosphorus or sulfur required to be externally added to support the growth and metabolism of microorganisms. Nutrients also include macrominerals such as calcium, sodium, magnesium and potassium.

A micronutrient is a trace metal or organic compound such as a vitamin or amino acid required in minute amounts for proper growth or metabolism of a microorganism.

Substantially steady-state means that although there may be variations, over time there is no material upward, or downward, trend. A steady-state bioconversion exists where the substrate, nutrients and micronutrients, and the production rate of hydrocarbonaceous compound are substantially stable.

Syngas means a gas, regardless of source, containing hydrogen and carbon monoxide and may, and usually does, contain carbon dioxide.

Overview

The processes of this invention for the anaerobic bioconversion of syngas to oxygenated hydrocarbonaceous compounds use a tight ultrafiltration membrane to enable a high portion of the water withdrawn from the fermentation for the recovery of oxygenated hydrocarbonaceous compounds, to be recycled to the fermentation without undue adverse effect on the microorganisms and to conserve nutrients, including micronutrients and enhance conversion efficiency of syngas to the oxygenated hydrocarbonaceous compounds in particular lower alkanol.

Syngas Bioconversions

Anaerobic fermentation to produce oxygenated hydrocarbonaceous compounds uses a substrate (syngas) comprising at least (i) carbon monoxide and (ii) carbon dioxide and hydrogen, the latter being for the hydrogen conversion pathway. Syngas can be made from many carbonaceous feedstocks. These include sources of hydrocarbons such as natural gas, biogas, biomass, especially woody biomass, gas generated by reforming hydrocarbon-containing materials, peat, petroleum coke, coal, waste material such as debris from construction and demolition, municipal solid waste, and landfill gas. Syngas is typically produced by a gasifier, reformer (steam, autothermal or partial oxidation). Any of the aforementioned biomass sources are suitable for producing syngas. The syngas produced thereby will typically contain from 10 to 60 mole % CO, from 10 to 25 mole % $CO_2$ and from 10 to 75, often at least about 30, and preferably between about 35 and 65, mole % $H_2$. The syngas may also contain $N_2$ and $CH_4$ as well as trace components such as $H_2S$ and COS, $NH_3$ and HCN. Other sources of the gas substrate include gases generated during petroleum and petrochemical processing and from industrial processes. The gas substrate may be obtained directly from gasification or from petroleum and petrochemical processing or industrial processes or may be obtained by blending two or more streams. Also, the gas substrate may be treated to remove or alter the composition including, but not limited to, removing components by chemical or physical sorption, membrane separation, and selective reaction. The syngas supplied to the bioreactor assembly contains at least about 10, preferably at least about 20, mole percent carbon monoxide and at least about 10, preferably at least about 20, mole percent hydrogen.

The oxygenated hydrocarbonaceous compoundss produced in the processes of this invention will depend upon the microorganism or combination of microorganisms used for the fermentation and the conditions of the fermentation. Bioconversions of CO and $H_2/CO_2$ to n-butanol, ethanol and other products are well known. For example, a concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds,. Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. Published Patent Application 20070275447, entitled "Indirect or Direct Fermentation of Biomass to Fuel Alcohol," which discloses a biologically pure culture of the microorganism *Clostridium* carboxidivorans having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to CO and used and this will enable the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 described in U.S. Pat. No. 8,143,037.

Pathways for the production of akanols having three carbons include, but are not limited to, *Propionibacterium* species (*Propionibacterium acidipropionici, Propionibacterium acnes, Propionibacterium cyclohexanicum, Propionibacterium freudenreichii, Propionibacterium freudenreichii shermanii, Propionibacterium pentosaecum*) and several other anaerobic bacteria such as *Desulfobulbus propionicus, Pectinatus frisingensis, Pelobacter propionicus, Veillonella, Selenomonas, Fusobacterium, Bacteroides fragile, Prevotella ruminicola, Megasphaera elsdenii, Bacteroides vulgates,* and *Clostridium*, in particular *Clostridium propionicum*.

Mixed cultures of anaerobic microorganisms useful for the bioconversions of syngas to alkanols as has been discussed above. The mixed cultures can be syntrophic and involve C1-fixing microorganisms and microorganisms that bioconvert the products to the C1-fixing microorganisms to higher alkanols. C1-fixing microorganisms include, without limitation, homoacetogens such as *Clostridium ljungdahlii, Clostridium autoethanogenum, Clostridium ragsdalei,* and *Clostridium coskatii*. Additional C1-fixing microorganisms include *Alkalibaculum bacchi, Clostridium thermoaceticum,* and *Clostridium aceticum*.

For instance, Enzien, et al., in United States Published Patent Application 20140206052 A1 disclose methods for producing butanol using C1-fixing homoacetogenic microorganisms and C4-producing butyrogens. See also, Datta, et al., United States Published Patent Application 20140206066 A1. Suitable butyrogens include any microorganisms that contain either or both of the BuCoAAT pathway and BuK pathway and can grow on acetate and ethanol or on acetate and hydrogen as typically found in syngas. Butyrogens known to grow exclusively on ethanol, acetate or syngas include *Clostridium kluyveri, Clostridium carboxidivorans,* and *Butyribacterium methylotrophicum*.

Syntrophic C3-producing microorganisms capable of growing on ethanol and/or acetate as their primary carbon source include, but are not limited to, *Pelobacter propionicus, Clostridium neopropionicum, Clostridium propionicum, Desulfobulbus propionicus, Syntrophobacter wolinii, Syntrophobacter pfennigii, Syntrophobacter fumaroxidans, Syntrophobacter sulfatireducens, Smithella propionica, Desulfotomaculum thermobenzoicum* subspecies *thermosymbioticum, Pelotomaculum the rmopropionicum,* and *Pelotomaculum schinkii*.

The aqueous fermentation broth will comprise an aqueous suspension of microorganisms and various media supplements. Suitable microorganisms generally live and grow under anaerobic conditions, meaning that dissolved oxygen is essentially absent from the fermentation broth. The various adjuvants to the aqueous fermentation broth may comprise buffering agents, trace metals, vitamins, salts etc. From time to time or continuously one or more streams of water, nutrients or adjuvants, and microorganisms are added to the fermentation broth. Adjustments in the fermentation broth may induce different conditions at different times such as growth and non-growth conditions which will affect the productivity of the microorganisms. U.S. Pat. No. 7,704,723 discloses the conditions and contents of suitable aqueous fermentation broth for bioconversion CO and $H_2/CO_2$ using anaerobic microorganisms.

The aqueous broth is maintained under anaerobic fermentation conditions including a suitable temperature, say, between 25° C. and 60° C., frequently in the range of about 30° to 40° C. The conditions of fermentation, including the density of microorganisms and aqueous fermentation broth composition are preferably sufficient to achieve the sought conversion efficiency of hydrogen and carbon monoxide. The pH of the aqueous broth is acidic, preferably less than about 6.5, and often between about 4 and 6.5.

The rate of supply of the feed gas under steady state conditions to a fermentation bioreactor is preferably such that the rate of transfer of carbon monoxide and hydrogen to the liquid phase matches the rate that carbon monoxide and hydrogen are bioconverted. The rate at which carbon monoxide and hydrogen can be consumed will be affected by the nature of the microorganism, the concentration of the microorganism in the aqueous fermentation broth and the fermentation conditions. As the rate of transfer of carbon monoxide and hydrogen to the aqueous fermentation broth is a parameter for operation, conditions affecting the rate of transfer such as interfacial surface area between the gas and liquid phases and driving forces are important. Preferably the feed gas is introduced into the bioreactor in the form of microbubbles. Often the microbubbles have diameters in the range of 0.01 to 0.5, preferably 0.02 to 0.3 millimeter.

The bioreactor assembly for syngas bioconversion may comprise one or more bioreactors which may be, with respect to gas flow, in parallel or in series flow. Each bioreactor may be of any suitable design; however, preferably the design and operation provides for a high conversion of carbon monoxide and hydrogen to oxygenated hydrocarbonaceous compounds. Fermentation reactors include, but are not limited to, bubble column reactors; jet loop reactors; stirred tank reactors; trickle bed reactors; biofilm reactors, including membrane bioreactors and membrane supported bioreactors; and static mixer reactors including, but not limited to, pipe reactors. Because of economy of capital cost and operation, deep tank bioreactors are preferred. Regardless of the type of deep tank bioreactor, especially where using microbubbles that promote a stable dispersion of bubbles in the aqueous broth, mixing currents exist that not only assure the relatively uniform aqueous phase composition but also increase the contact time between the gas bubbles and the aqueous broth.

The substrate depleted gas phase egressing from the aqueous fermentation broth will contain a small fraction of the hydrogen and carbon oxides introduced into the bioreactor assembly as the feed gas. Inerts such as nitrogen and primarily methane will comprise a portion of the depleted gas phase where syngas from steam reforming or oxygen-fed, autothermal reforming, especially steam or autothermal reforming of methane-containing gas, is used. The depleted gas phase may also contain sulfur-containing compounds, alcohol and the like volatilized from the aqueous fermentation broth.

OHC Recovery and Water and Nutrient Recycle

A portion of the aqueous fermentation broth is withdrawn from time to time or continuously from the bioreactor for recovery of the oxygenated hydrocarbonaceous compounds. The invention applies to those cases where the OHC is recoverable using a distillation unit operation where an oxygenated hydrocarbonaceous compound-containing fraction and an aqueous distillation fraction are obtained. Product recovery can also consist of other known equipment arrangements to assist in the removal of one or more of residual cell material, separation and recovery of liquid products from the fermentation liquid, return of recovered fermentation liquid and purging of waste streams and materials. These other equipment arrangements can include filters, centrifuges, cyclones, membrane systems and other separation equipment. U.S. Pat. No. 8,211,679 shows an arrangement for a product recovery bioreactor that recovers an ethanol product from a bioreactor.

The aqueous fermentation broth withdrawn from the bioreactor contains microorganisms, fragments of microorganisms, nutrients and micronutrients, unreacted substrate, OHC, and lower carboxylate anion. If desired, the concentration of lights such as hydrogen, carbon monoxide, carbon dioxide, nitrogen, and methane in the withdrawn broth can be reduced, e.g., through a flash unit operation prior to the broth being introduced into the distillation unit operation. In some instances, the withdrawn broth is subjected to one or more solids removal unit operations to reduce or substantially eliminate the presence of microorganisms prior to passing to the distillation unit operation. If desired, at least a portion of the separated microorganisms can be recycled to the bioreactor. See, for instance, United States Published Patent Application 20130137151 A1. However, a microorganism-containing broth can be introduced into the distillation unit operation. The temperatures used in the distillation serve to denature the broth and can result in the fragmentation of cells, including the increased presence of proteins.

The distillation unit operation can comprise one or more distillation columns and ancillary equipment. The configuration of the distillation unit operation will depend upon the oxygenated hydrocarbonaceous compounds being recovered as the product as is known in the art. The distillation unit operation provides an OHC-rich fraction and an aqueous distillation fraction. The aqueous distillation fraction contains solids which include the denatured microorganisms and solid fragments and dissolved components including, but not limited to nutrient, including micronutrients, and carboxylate anion.

A portion of the aqueous distillation fraction may optionally be recycled to the bioreactor. Typically, this recycled portion is an aliquot portion although it may be subjected to unit operations such as solids separation that may alter the overall composition but not the liquid composition of the recycled portion. Often, where used, the recycled portion comprises at least about 50, say, between about 50 and 90, preferably between about 60 and 85, percent of the water in the aqueous distillation fraction.

In some instances, especially where the concentration of solids in the liquid discharge is about 25 milligrams per liter or less, it may not be necessary to separate the solids prior to being passed to the ultrafiltration unit operation. Preferably the solids are removed, e.g., to a concentration of less than about 5, and most frequently less than about 1, milligrams per liter. The solids removal may be any suitable unit operation, preferably a unit operation using the differential in densities for separation, such as settling, centrifugation and hydrocyclone unit operations. Filtration unit operations such as microfiltration can be used alone or in combination with a density separation unit operation. The low solids content typically results in only a small portion of the liquid phase remaining with the solids-rich fraction, e.g., less than about 10, preferably less than about 5 and as low as 1 or even less in some instances, volume percent of the aqueous distillation fraction. As can be readily appreciated, the operator has the flexibility to balance the efficiency of the solids separation and energy consumption against the value of nutrients and carboxylate anion lost with the solids-rich fraction and maintenance of the ultrafiltration membrane.

Where one or more of a recycle of a portion of the aqueous distillation fraction and a solids separation unit operation occurs, the remaining portion of the aqueous distillation fraction is the liquid discharge.

At least a portion of the liquid discharge is subjected to ultrafiltration using an ultrafiltration membrane having a cut-off in the range of between about 750 to 8000, preferably between about 800 and 7500, Daltons. Any suitable ultrafiltration membrane design may be used, including hollow fiber, spiral wound and flat plate. Any suitable ultrafiltration conditions can be used. Often the temperature is in the range of between about 10° C. to 60° C., and the pressure on the retentate side of the ultrafiltration membrane is between about 200 and 2000, say, 500 to 1500, kPa absolute, with a pressure drop of between 100 and 2000, say, 200 to 1500, kPa. The flux of water through the ultrafiltration membrane will be influenced by the design of the membrane itself and the pressure differential across the membrane. Thus, the membrane surface area and pressure differential can be selected for a given type of membrane to achieve a sought amount of the water being recovered on the permeate side for recycle to the bioreactor. In accordance with the processes of this invention, at least 75 percent of the water contained in the liquid discharge is contained in the permeate. Most preferably at least about 85, and in some instances, at least about 90, percent of the water passes to the permeate side during ultrafiltration. Thus a substantial amount of the water in the aqueous fermentation broth withdrawn from the bioreactor can be recycled.

A large portion of the nutrients and micronutrients are recycled with the permeate and, if used, the optional aliquot recycle. Even where unit operations are conducted to recover nutrients, such as nitrogen and sulfur-containing nutrients, from the retentate and the solids-containing fraction, the permeate and the optional recycle will provide a greater amount of these nutrients than such other unit operations.

Where an aliquot portion of the aqueous distillation fraction is recycled and the remaining portion is subjected to ultrafiltration, high water recycle rates can be achieved, e.g., at least about 80, preferably at least about 90, and in some instances at least about 95, percent of the water in the withdrawn fermentation broth is recycled. In some instances, where the feed gas contains a high mole fraction of hydrogen, e.g., a hydrogen to carbon monoxide mole ratio of greater than 2, water is generated by the bioconversion and thus reduces water usage such that little if any, water needs to be added to the bioreactor to compensate for purge loses.

As stated above, the permeation rates of other components in the liquid discharge are dependent upon the permeation rate of each of those components. By using an ultrafiltration membrane having a cut-off of up to about 8000 Daltons, a predominant portion of the components that can adversely affect the microorganisms are rejected. Using an ultrafiltration membrane having a cut-off of 10,000 Daltons enables over twice as much protein to permeate as compared to that using an ultrafiltration membrane having a 5000 Dalton cut-off. Lower carboxylate anion and nutrients and micronutrients are able to pass through ultrafiltration membranes having a cut-off of 750 or more Daltons. Since a large portion of the water permeates, the mass percentage of these components in the permeate based upon the amount in the liquid discharge, is substantial, even if the concentration of a component in the permeate is less than that in the liquid discharge. For instance, if the concentration of a component in the permeate is 75 percent of that in the liquid discharge, and 75 percent of the water is passed to the permeate, 56 percent of that component is contained in the permeate and available for recycle to the bioreactor.

In the preferred aspects of this invention, the permeate has a concentration of each of the potassium and ammonium cations of at least about 90 percent of that in the liquid discharge, and a concentration of sulfur and phosphorus-containing components of at least about 70 mass percent of that in the liquid discharge. In comparison, the concentration of proteins in the permeate is less than about 20 mass percent of that in the discharge, and of total sugars, is less than about 35 mass percent of that in the liquid discharge. Table 1 sets forth preferred ranges and more preferred in parentheses for the concentration of a component in the permeate (Percent Comparison) as compared to the liquid discharge passed to the ultrafiltration and total recovery of the component in the permeate (Total Recovery).

TABLE 1

| Component | Percent Comparison, % | Total Recovery, mass % |
|---|---|---|
| Zn | >80 (>85) | >60 (>75) |
| Se | >70 (>75) | >50 (>65) |
| S | >70 (>75) | >50 (>65) |
| P | >70 (>75) | >50 (>65) |
| Ni | >60 | >45 (>55) |
| Na | >90 (>95) | >65 (>90) |
| Mo | >60 | >45 (>55) |
| Mn | >70 (>75) | >50 (>65) |
| Mg | >60 | >45 (>55) |
| K | >90 (>95) | >65 (>90) |
| Fe | >40 | >30 (>35) |
| Co | >60 | >45 (>55) |
| Ca | >70 (>75) | >50 (>65) |
| Carboxylate | >75 (>80) | >60 (>75) |
| Ammonium | >90 (>95) | >65 (>90) |
| Sugars | <35 (<25) | <35 (<25) |
| Protein | <20 (<15) | <20 (<15) |

At least about 90 volume percent, and preferably all, of the permeate is recycled to the bioreactor. In some instances where multiple bioreactors are being used, the recycled permeate can be passed to one or more of the bioreactors, and if more than one, in different amounts. The retentate fraction is typically passed to wastewater treatment or otherwise disposed.

In one aspect of this invention, nutrients, including micronutrients, can be recovered from solids-containing fractions from the process. For instance, the separation of microorganisms and solids from any solids removal unit operation up-stream or downstream from the distillation unit operation can be subjected to anaerobic digestion to produce methane and an aqueous discharge. At least a portion of the discharge from the anaerobic digestion can be passed to the ultrafiltration unit operation for water and nutrient recovery. Preferably the discharge from the anaerobic digestion is subjected to a solids removal unit operation and is passed to wastewater treatment or otherwise disposed.

Drawings

A general understanding of the invention and its application may be facilitated by reference to FIG. 1. FIG. 1 is a schematic depiction of an apparatus generally designated as 100 suitable for practicing processes in accordance with this invention for the production and recovery of ethanol. The invention can be operated in either continuous or batch mode. Both are described below. FIG. 1 omits minor equipment such as pumps, compressors, valves, instruments, the exchangers and other devices the placement of which and the operation thereof are well known to those practiced in chemical engineering. FIG. 1 also omits ancillary unit operations. The processes and operation of FIG. 1 will be described in the context of the recovery and production of ethanol. The process is readily adaptable to processes for making other oxygenated hydrocarbonaceous compounds.

Syngas is provided to fermentation reactor 104 via line 102. Fermentation reactor 104 is adapted to hold an aqueous fermentation broth and microorganisms for bioconverting syngas to ethanol. Fermentation reactor 104 is adapted to be operated on a continuous basis. An off gas, which typically contains nitrogen, methane, and unreacted hydrogen, carbon dioxide and carbon monoxide, is withdrawn from fermentation reactor 104 via line 106. All, or a portion of the off-gas in line 106 is directed via line 108a for further processing to increase heating value as will be described later. Make-up water and nutrients are added to fermenter 104 via line 105 as required.

A portion of the aqueous fermentation broth in fermentation reactor 104 is withdrawn via line 110, heated in heat pump assembly 112, and then passed via line 114 to distillation assembly 116. Heat pump assembly comprises indirect heat exchangers from which a heat pump removes heat or into which the heat pump introduces heat. Fermentation broth is withdrawn from fermentation reactor 104 via line 118 and cooled in heat pump assembly 112 and returned via line 120 to fermentation reactor 104. Thus heat from the exothermic fermentation is removed and is used to increase the temperature of the aqueous fermentation broth passing to distillation assembly 116 which in turn reduces the heat required to be supplied by other unit operations (not shown) in the distillation assembly for the distillation assembly while concurrently decreasing external cooling requirements of the broth in fermenter 104.

Distillation assembly 116 separates ethanol from the aqueous phase and provides an ethanol rich product which is withdrawn via line 124. Non-condensables exit distillation assembly 116 via line 122. The heat in the distillation assembly 116 kills the microorganisms used for the bioconversion of syngas. A bottoms stream (aqueous distillation fraction) containing solids from the microorganisms and proteins precipitated from solution in an aqueous phase is passed via line 126 to a solids separation unit operation 128, which for purposes of discussion is a centrifuge. The solids depleted fraction is withdrawn from the centrifuge is via line 130. As shown, an aliquot portion is recycled to fermentation reactor 104 via line 130a and the remaining portion, the liquid discharge, is directed to ultrafiltration assembly 132 via line 130b. The solids fraction from solids separation unit operation 128 is transported via line 134 to anaerobic digester 136.

Anaerobic digester 136 generates a biogas comprising methane and reduces the solids generated by the fermentation. As shown, all or a portion of the off-gas from fermentation reactor 104 is passed to anaerobic digester 136 via lines 108a which is in fluid communication with line 108b (not shown). The off-gas contains unreacted carbon dioxide, hydrogen and carbon monoxide that can be bioconverted to methane in anaerobic digester 136. Thus, the biogas produced by the anaerobic digestion will have a higher energy density than the off-gas from the fermentation reactor. In one embodiment the introduction of the off-gas has an additional advantage. The carbon dioxide contained in the off-gas is of sufficient mass such that it serves to lower the pH in the anaerobic digestion. This lower pH results in reducing the undissociated ammonia, and in many instances, the concentration of undissociated ammonia can be maintained below those inhibitory to the microorganisms effecting the digestion. Often the digestion can result in approximately 40 to 50 mass percent of the biosolids and precipitated protein being bioconverted to ammonium cation in the anaerobic digester.

Biogas generated in anaerobic digester 136 is passed via line 138 to biogas scrubber 140 to remove hydrogen sulfide. Biogas scrubber uses an activated sludge-containing aqueous medium from an aerobic wastewater treatment facility which is supplied via line 144. A spent scrubbing liquor is withdrawn from biogas scrubber via line 146. The spent scrubbing liquor can be returned to an aerobic treatment unit where the sulfide is oxidized to sulfate and/or elemental sulfur. A biogas having a reduced sulfur content exits biogas scrubber via line 142. The biogas can be combusted to generate heat or flared for disposal.

Returning to anaerobic digester 136, an aqueous solution containing the digested solids is withdrawn via line 150 and is passed to solids separation unit operation 154, which for purposes of discussion herein, is a centrifuge. Solids separation unit operation provides a liquor phase which all or a portion can be directed via line 156 to ultrafiltration assembly 132, and the remaining portion of the liquor phase can be directed via line 157 to ammonia stripper 164. A solids-containing stream from solids separation unit operation 154 is passed via line 166 further treatment, use or disposal. The liquid phase from 154 contains on the order of 40 to 50% of the nitrogen in the wasted biosolids and precipitated proteins as dissolved ammonium. By processing this stream in ultrafiltration assembly 132 this ammonium can be returned back to the fermentation significantly reducing the amount of nitrogen that needs to be added exogenously to the fermenter as purchased N.

Ultrafiltration assembly 132 contains an ultrafiltration membrane. For purposes of this discussion, the ultrafiltration membrane has a cut-off of about 1 kiloDalton, but it should be understood that ultrafiltration membranes with cut-offs within the range of 750 and 8000 Daltons can find application. The portion of the water that passes through the ultrafiltration membrane can vary depending upon operator preferences. Where the ultrafiltration assembly is used to recover about 94 percent of the water in the liquid discharge, the ultrafiltration rejects about 73 mass percent of the sugars and over 85 mass percent of the proteins in the liquid discharge. Table 2 reports the concentration of the identified component, as a percentage of that component in the feed to the ultrafiltration membrane assembly.

TABLE 2

| Component | Concentration in permeate as compared to feed on a percentage basis |
|---|---|
| Zn | 88 |
| Se | 78 |
| S | 80 |
| P | 83 |
| Ni | 69 |
| Na | 96 |
| Mo | 66 |
| Mn | 80 |
| Mg | 73 |
| K | 101 |
| Fe | 48 |
| Co | 72 |
| Ca | 80 |
| Acetic acid | 91 |
| Ammonium ion | 98 |
| Sugars | 27 |
| Proteins | 14 |

In comparison, a 10 kiloDalton cut-off ultrafiltration membrane provides a permeate with a concentration of about 48 percent of the proteins and 38 percent of the sugars of that in the feed to the ultrafiltration assembly.

The permeate is passed via line 158 to fermentation reactor 104. The small pore size of the ultrafiltration membrane results in the membrane resisting fouling by solids.

The permeate contains nutrients and micronutrients and acetate anion but has a low concentration of proteins and metabolites. If desired, the retentate can be passed via line 160 to ammonia stripper 164. In many instances, the amount of ammonium cation contained in the retentate does not justify further treatment and it can be passed to satewater treatment. All, or a portion, of the retentate can be recycled via line 162 to line 134 and anaerobic digester 136. Alternately some or all of the retentate can be directed via line 163 to wastewater treatment via line 166

In most instances, it is preferred to pass the anaerobic digestion liquor via line 156 to the ultrafiltration unit operation to recycle the ammonium cation to fermentation reactor 104. However, if desired, all or a portion of the anaerobic digestion liquor can be passed to ammonia stripper 164 together with all or a portion of the retentate from the ultrafiltration assembly 132. carbon dioxide can be stripped from the liquid from the anaerobic digestion to result in an increase in the pH of the liquid and a release of undissociated ammonia for recovery. The liquids passed to ammonia stripper 164 are heated such that carbon dioxide and ammonia are stripped. Since the stripping of carbon dioxide increases the pH, undissociated ammonia is generated and can be stripped. The stripping may be achieved using a typical stripping tower using air as the stripping gas, steam stripping, a vacuum membrane contactor (with or without sweep gas) or vacuum stripping. The stripped liquor is removed from ammonia stripper 164 via line 170 and can be discharged or sent to an aerobic digester. Line 168 provides stripping gas to ammonia stripper 164. The stripped gas is passed from ammonia stripper 164 to ammonia absorption column 174 via line 172. Water for the ammonia absorption column circulates via loop 178, and a purge is take via line 176 which contains undissociated ammonia and ammonium carbonate which can be used as a source of nitrogen nutrient or as a product stream. Water replenishment, if needed, is provided by line 180.

It is claimed:

1. A continuous process for the anaerobic bioconversion of a gas substrate comprising carbon monoxide, hydrogen and carbon dioxide in an aqueous broth containing microorganisms suitable for converting said substrate to oxygenated hydrocarbonaceous compound, which process comprises:
   a. continuously contacting said gas substrate with said aqueous broth under acidic, anaerobic fermentation conditions including the presence of nutrients to bioconvert gas substrate to oxygenated hydrocarbonaceous compound and provide an oxygenated hydrocarbonaceous compound-containing broth and a depleted gas phase, said anaerobic fermentation conditions also producing a co-produced, lower carboxylate anion and metabolites adverse to said microorganisms;
   b. continuously withdrawing the depleted gas phase from said aqueous broth;
   c. continuously or intermittently withdrawing a portion of said aqueous broth for recovery of said oxygenated hydrocarbonaceous compound, said withdrawal being sufficient to maintain the oxygenated hydrocarbonaceous compound in said aqueous broth below a concentration that unduly adversely affects the microorganisms;
   d. continuously separating by distillation the oxygenated hydrocarbonaceous compound from the withdrawn portion of said aqueous broth to provide an oxygenated hydrocarbonaceous compound fraction rich in said oxygenated hydrocarbonaceous compound and an aqueous distillation fraction containing said co-produced, lower carboxylate anion and said adverse metabolites, wherein said distillation denatures said aqueous broth and generates free proteins;
   e. optionally recycling a portion of the aqueous distillation fraction to step (a);
   f. subjecting a portion of the aqueous distillation fraction to ultrafiltration to permeate at least about 75 percent of the water contained in said subjected portion, said ultrafiltration using an ultrafiltration membrane having a cut-off in the range of between 750 and 8000 Daltons to provide permeate including said co-produced, lower carboxylate anion; and
   g. recycling the permeated of step (f) to step (a).

2. The process of claim 1 wherein solids are removed prior to being passed to step (d) and/or prior to being passed to step (e) or step (f).

3. The process of claim 2 wherein the ultrafiltration membrane has a cut-off between about 800 and 7500 Daltons.

4. The process of claim 3 wherein at least about 85 percent of the water in the portion of the aqueous distillation fraction subjected to ultrafiltration is permeated in step (f).

5. The process of claim 3 wherein the aqueous distillation fraction contains potassium and ammonium anion and the permeate has a concentration of each of the potassium and ammonium cations of at least about 90 percent of that in the portion of the aqueous distillation fraction subjected to ultrafiltration.

6. The process of claim 3 wherein the aqueous distillation fraction contains sulfur and phosphorus-containing components and the permeate has a concentration of each of the sulfur and phosphorus-containing components of at least about 70 mass percent of that in the portion of the aqueous distillation fraction subjected to ultrafiltration.

7. The process of claim 3 wherein the concentration of proteins in the permeate is less than about 20 mass percent of that in the portion of the aqueous distillation fraction subjected to ultrafiltration.

8. The process of claim 7 wherein at least about 60 percent of the lower carboxylate anion in the portion of the aqueous distillation fraction subjected to ultrafiltration is contained in the permeate of step (f).

9. The process of claim 2 wherein the solids removed are subjected to anaerobic digestion to produce methane and an aqueous discharge, subjecting the aqueous discharge to a solids removal unit operation to provide an aqueous liquor and a solids-rich fraction, and passing at least a portion of the aqueous liquor to step (f).

10. The process of claim 1 wherein oxygenated hydrocarbonaceous compound is a oxygenated hydrocarbon.

11. The process of claim 10 wherein the oxygenated hydrocarbon is a lower alkanol.

12. A continuous process for the anaerobic bioconversion of a gas substrate comprising carbon monoxide, hydrogen and carbon dioxide in an aqueous broth containing microorganisms suitable for converting said substrate to lower alkanol, which process comprises:
   a. continuously contacting said gas substrate with said aqueous broth under acidic, anaerobic fermentation conditions including the presence of nutrients to bioconvert gas substrate to lower alkanol and provide a lower alkanol-containing broth and a depleted gas phase, said anaerobic fermentation conditions also producing a co-produced, lower carboxylate anion and metabolites adverse to said microorganisms;

b. continuously withdrawing the depleted gas phase from said aqueous broth;

c. continuously or intermittently withdrawing a portion of said aqueous broth for recovery of said lower alkanol, said withdrawal being sufficient to maintain the lower alkanol in said aqueous broth below a concentration that unduly adversely affects the microorganisms;

d. continuously separating by distillation the lower alkanol from the withdrawn portion of said aqueous broth to provide an alkanol fraction rich in said lower alkanol and an aqueous distillation fraction containing said co-produced, lower carboxylate anion and said adverse metabolites, wherein said distillation denatures said aqueous broth and generates free proteins;

e. optionally recycling a portion of the aqueous distillation fraction to step (a);

f. subjecting a portion of the aqueous distillation fraction to ultrafiltration to permeate at least about 75 percent of the water contained in said subjected portion, said ultrafiltration using an ultrafiltration membrane having a cut-off in the range of between 750 and 8000 Daltons to provide permeate including said co-produced, lower carboxylate anion; and g. recycling the permeated of step (f) to step (a).

13. The process of claim 12 wherein solids are removed prior to being passed to step (d) and/or prior to being passed to step (e) or step (f).

14. The process of claim 13 wherein the ultrafiltration membrane has a cut-off between about 800 and 7500 Daltons.

15. The process of claim 14 wherein at least about 85 percent of the water in the portion of the aqueous distillation fraction subjected to ultrafiltration is permeated in step (f).

16. The process of claim 14 wherein the aqueous distillation fraction contains potassium and ammonium anion and the permeate has a concentration of each of the potassium and ammonium cations of at least about 90 percent of that in the portion of the aqueous distillation fraction subjected to ultrafiltration.

17. The process of claim 14 wherein the aqueous distillation fraction contains sulfur and phosphorus-containing components and the permeate has a concentration of each of the sulfur and phosphorus-containing components of at least about 70 mass percent of that in the portion of the aqueous distillation fraction subjected to ultrafiltration.

18. The process of claim 14 wherein the concentration of proteins in the permeate is less than about 20 mass percent of that in the portion of the aqueous distillation fraction subjected to ultrafiltration.

19. The process of claim 18 wherein at least about 60 percent of the lower carboxylate anion in the portion of the aqueous distillation fraction subjected to ultrafiltration is contained in the permeate of step (f).

20. The process of claim 13 wherein the solids removed are subjected to anaerobic digestion to produce methane and an aqueous discharge, subjecting the aqueous discharge to a solids removal unit operation to provide an aqueous liquor and a solids-rich fraction, and passing at least a portion of the aqueous liquor to step (f).

* * * * *